United States Patent [19]

Arai et al.

[11] Patent Number: 5,763,583
[45] Date of Patent: Jun. 9, 1998

[54] PROCESS FOR PRODUCING SOLUBILIZED PROTEIN

[75] Inventors: Kozo Arai, Gunma; Hiroshi Nojiri, Tochigi; Sachio Naito, Ibaraki, all of Japan

[73] Assignee: Kao Corporation, Tokyo, Japan

[21] Appl. No.: 540,318

[22] Filed: Oct. 6, 1995

Related U.S. Application Data

[63] Continuation of Ser. No. 248,244, May 24, 1994, abandoned.

[30] Foreign Application Priority Data

May 24, 1993 [JP] Japan ................... 5-142516

[51] Int. Cl.⁶ ................................... A61K 38/17
[52] U.S. Cl. ................ 530/353; 530/356; 530/357; 530/408; 530/410; 530/417
[58] Field of Search ................... 530/353, 356, 530/357, 408, 410, 417

[56] References Cited

U.S. PATENT DOCUMENTS

| | | | |
|---|---|---|---|
| 4,652,630 | 3/1987 | Bentle et al. | 530/344 |
| 4,694,073 | 9/1987 | Bentle et al. | 530/399 |
| 4,731,440 | 3/1988 | Bentle et al. | 530/399 |
| 4,985,544 | 1/1991 | Yokoo et al. | 530/399 |
| 5,240,834 | 8/1993 | Frankel et al. | 435/71.2 |

FOREIGN PATENT DOCUMENTS

WO-A8702985  5/1987  WIPO .

OTHER PUBLICATIONS

Menkart et al, *3rd International Wool Textile, Research Conference Proceedings*, vol. 2, pp. 329–336, 1965.
Menkart et al. *Chemical Abstracts*, vol. 67, p. 8000, Ref. #84763v, 1967.
Yamashita et al. *The Journal of Biological Chemistry*, vol. 268, No. 25, pp. 19062–19069, Sep. 5, 1993.
Chemical Abstracts, "Mechanical properties of regenerated keratin films prepared from thioglycolic acid solution of wool proteins", vol. 118, No. 18, 3 May 1993, p. 129.
Chemical Abstracts, "Production of Low–molecular weight keratin", vol. 97, No. 22, 29 Nov. 1982, p. 371.

*Primary Examiner*—Cecilia J. Tsang
*Assistant Examiner*—Abdel A. Mohamed
*Attorney, Agent, or Firm*—Sughrue, Mion, Zinn, Macpeak & Seas, PLLC

[57] ABSTRACT

A process for the production of a solubilized protein is disclosed, which is obtained by reducing disulfide bonds in a disulfide bond-containing water-insoluble protein material into mercapto groups and subsequently converting a part or an entire portion thereof into carboxymethyldisulfide groups. In particular, the disclosed process for the production of a solubilized protein which comprises (a) treating a disulfide bond-containing water-insoluble protein material with an aqueous alkaline solution of a reducing agent, and (b) reacting the protein treated by step (a) with thioglycolic acid in the presence of an oxidizing agent under a weakly acidic to a weakly alkaline condition. A process for the production of regenerated protein products, which comprises regenerating disulfide bonds in the solubilized protein, is also disclosed.

5 Claims, 2 Drawing Sheets

PROCESS FOR PRODUCING SOLUBILIZED PROTEIN

This is a Continuation of application Ser. No. 08/248,244, filed on May 24, 1994, abandoned.

FIELD OF THE INVENTION

This invention relates to a process for solubilizing water-insoluble and disulfide bond-containing proteins derived from wool and other like animal hair, human hair, and other like protein-containing materials. In addition, it relates to a novel process for regenerating solubilized protein for use in regenerated protein products, such as regenerated protein films and regenerated protein fibers.

BACKGROUND OF THE INVENTION

As is well known, keratin fibers, such as those found in wool, feel rich due to their excellent hygroscopic and moisture releasing properties, which respond to the moisture content of the air. Such properties are characteristic of a complex composed of a fibrous keratin with α-helix structure, which is the crystalline moiety of the fiber, and an amorphous matrix protein, the molecules of which are cross-linked with each other through disulfide bonds (—SS—).

Attempts have been made to solubilize keratin fibers having these excellent physical properties in order to recycle them. For example, a process is known in which an aqueous solution of sodium thioglycolate is treated with an oxidizing agent in order to improve the reducing power of thioglycolic acid. The resulting partially oxidized aqueous solution of sodium thioglycolate, which is partially converted into sodium thiodiglycolate, is then applied to feathers to produce an aqueous solution of keratin having high viscosity and high molecular weight (JP-A-53-119900; the term "JP-A" as used herein means an "unexamined published Japanese patent application"). A process is also known in which wool is solubilized by treating it with 100% thioglycolic acid under heating (JP-A-4-91138). Another process is known in which a keratin membrane is toughened and softened by addition of an aliphatic polyhydric alcohol (JPB-55-33826; the term "JP-B" as used herein means an "examined Japanese patent publication"). Finally, a process is known in which wool is treated with a reducing agent, the resulting mercapto group-containing protein is dissolved in a neutral buffer solution, and a protein film for use as a cell culture bed is formed from the solution by forming disulfide bonds or cross-linking bonds with UV irradiation (JP-A-60-160883).

However, all of these conventional processes are disadvantageous as the protein solubilization methods used convert disulfide bonds into mercapto groups by means of reduction. Protein fibers, such as those in wool, have a low solubilization ratio because of their high disulfide bond crosslinking density. Solubilized proteins in which mercapto groups remain as such are not easily dissolved in neutral aqueous solutions. In addition, they easily form disulfide bonds by oxidation with air, and thereby become insoluble in water.

When a severe treatment (e.g., heat treatment) is used to increase the solubilization ratio, protein decomposition occurs.

The process described in JP-A-4-91138 has the disadvantage that the viscosity of the resulting solution decreases, which indicates formation of low molecular weight protein molecules.

SUMMARY OF THE INVENTION

An object of the present invention is to develop techniques which are effective not only in solubilizing animal fiber proteins having high disulfide bond crosslinking density, but also to: (1) maintain the molecular weight and the α-helix primary structure of the keratin protein in the solubilized protein without substantial cleaving of peptide bones; (2) attain a high protein solubility in water; and (3) develop solubilized proteins capable of forming a disulfide bond cross-linked structure for use in regenerated protein products.

The present inventors have conducted extensive studies with the aim of overcoming the disadvantages of conventional processes. As a result, it has now been discovered that when keratinized tissues, such as animal and human hair (e.g., wool, feathers), hooves, and other like materials containing keratin protein that is water-insoluble due to the existence of disulfide bonds, are treated with a thioglycolic acid aqueous solution to reduce disulfide bonds, and the resulting product is oxidized in the presence of thioglycolic acid to form a mixed disulfide (carboxymethyldisulfide), the resulting protein dissolves in water.

The present invention provides a process for the production of solubilized protein that comprises:

(a) treating a disulfide bond-containing water-insoluble protein material with an aqueous alkaline solution of a reducing agent; and (b) reacting the disulfide bond-containing water-insoluble protein material from step (a) with thioglycolic acid in the presence of an oxidizing agent under a weakly acidic to a weakly alkaline condition.

The present invention further relates to a process for the production of a regenerated protein product, which comprises forming the solubilized protein obtained in the process described above into a desired shape, and then regenerating disulfide bonds in the protein.

DETAILED DESCRIPTION OF THE INVENTION

Figure 1:
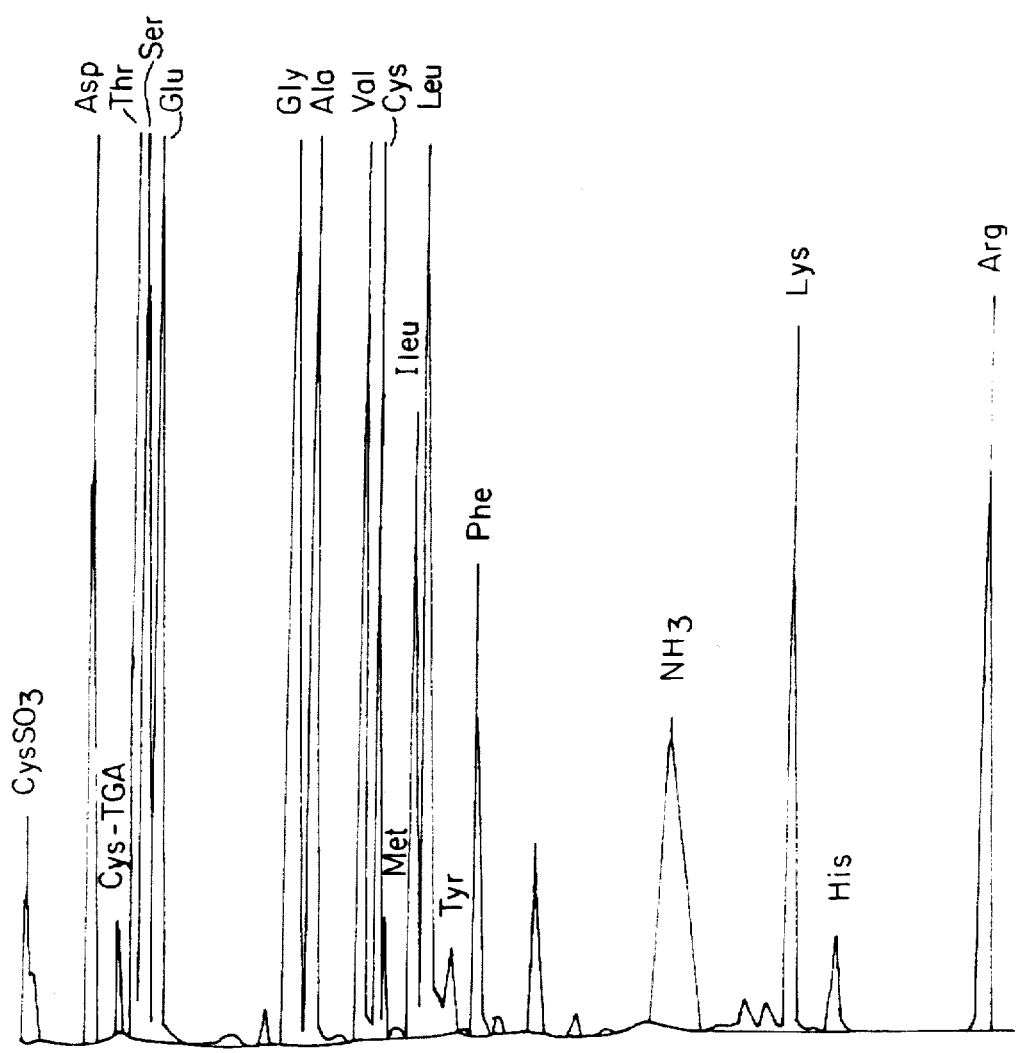
FIG. 1 is a graph showing an amino acid composition of a solubilized wool keratin protein.

In accordance with the present invention, disulfide bonds (—SS—) in the disulfide bond-containing water-insoluble protein are reduced into mercapto groups (—SH) and a part or entire portion of the mercapto groups is subsequently converted into carboxymethyldisulfide groups (—SSCH$_2$COOH), whereby the solubilized protein is obtained.

Examples of disulfide bond-containing water-insoluble proteins used in the present invention include natural keratin proteins of animal hair, feathers, hooves, horns, claws, and other like proteins. Though not particularly limited, illustrative examples of animal hair include wool of Merino, Lincoln, and other like breeds of sheep, and human hair.

The water-insoluble protein material is chopped up, or pulverized, if desired, and then reduced by soaking it in an aqueous alkaline solution of a reducing agent.

Any reducing agent may be used in the reduction, provided that it dissolves in water. Preferred examples of reducing agents include thioglycolic acid and a salt thereof, thiolactic acid and a salt thereof, thioglycerol, dithiothreitol, 2-mercaptoethanol, cysteamine, glutathione, thiourea, tri-n-butylphosphine, sodium borohydride and the like, of which thioglycolic acid and a salt thereof are particularly preferred. Specific examples of the salts of thioglycolic acid and thiolactic acid include the ammonium salt, sodium salt and potassium salt.

The amount of the reducing agent to be used is estimated from the number of disulfide bonds in the water-insoluble protein, which is calculated by mercapto group measurement. In general, it is used in an amount of from 0.0005 to 5 mole, preferably from 0.005 to 0.05 mole, per 1 g of water-insoluble protein. The concentration of the reducing agent in the aqueous solution is preferably from 0.01 to 10M, preferably from 0.1 to 1M.

When thioglycolic acid is used as the reducing agent, it may be used in an amount that is sufficient not only for the reduction of disulfide bonds in the water-insoluble protein into mercapto groups, but also for the subsequent formation of carboxymethyldisulfide by oxidation.

The pH value of the aqueous alkaline solution of the reducing agent may preferably range from 7 to 13, more preferably from 9 to 12. When an acid is used as the reducing agent, the pH value of the aqueous solution may be adjusted with one or more alkali agents, which may be selected preferably from potassium hydroxide, sodium hydroxide, ammonia, monoethanolamine, and diethanolamine, as well as from basic amino acids (e.g., arginine and lysine), sodium bicarbonate, ammonium bicarbonate and the like. However, the kind of alkali agent is not particularly limited.

If desired, a protein denaturing agent may be used after the reduction step. An aqueous solution of 2 to 8M urea or 2 to 5M guanidine hydrochloride may be used as the protein denaturing agent. Treatment with a protein denaturing agent may be carried out by soaking the reduced water-insoluble protein in an aqueous protein denaturing solution at 0° to 40° C. for 1 to 48 hours with stirring.

After completion of the reduction reaction, and optional treatment with a protein denaturing agent, the protein and thioglycolic acid are reacted with each other in the presence of an oxidizing agent. When thioglycolic acid is used as the reducing agent in the reduction treatment and it still remains in the reaction system in a sufficient amount, it can be used in this oxidation reaction.

When a reducing agent other than thioglycolic-acid is used in the reduction treatment, the reduction-treated protein is collected by filtration to remove the reducing agent solution, and then soaked in a thioglycolic acid aqueous solution.

Thioglycolic acid may be used in such an amount that mercapto groups in the water insoluble protein can be converted into carboxymethyldisulfide by oxidation. In general, it is used in an amount of from 0.0005 to 0.5 mole, preferably from 0.005 to 0.05 mole, per 1 g of protein. The concentration of thioglycolic acid in the reaction system is preferably from 0.01 to 10M, more preferably from 0.1 to 1M.

The reaction of protein with thioglycolic acid may be carried out by adjusting the pH of the solution with an acid to a weakly acidic to a weakly alkaline value, preferably in the range of from pH 5 to 9, more preferably from pH 6 to 8. The acid is not particularly limited, and may be selected from organic acids such as acetic acid, lactic acid, citric acid, and succinic acid, and inorganic acids such as phosphoric acid.

Though not particularly limited, the oxidizing agent may be selected from oxygen, sodium bromate, potassium bromate, hydrogen peroxide, and the like.

The oxidation reaction may be carried out at 0° to 40° C. by bubbling oxygen into the reaction system or by adding an aqueous solution of one of the aforementioned oxidizing agents. The oxidation reaction is complete when mercapto-originated odor becomes undetectable, or when the disappearance of mercapto groups is confirmed by adding an appropriate amount of a sample collected from the reaction solution to a neutral aqueous solution of 0.1M sodium dinitrobisbenzoate and measuring absorbance of the resulting mixture at 412 nm.

If necessary, the thus obtained solubilized protein may be further purified by an appropriate purification. For example, oxidization products of the reducing agent and the protein denaturing agent, such as urea, low molecular weight polypeptides, electrolytes, and the like, can be removed by subjecting the solubilized protein aqueous solution to a method of dialysis, such as electrodialysis. If desired, insoluble materials may be removed by means of filtration or centrifugation.

The solubilized protein obtained in the process of the present invention has the following properties.

(1) Amino acid analysis:

Carboxymethyldisulfide bonds which do not originally exist in the wool protein are formed in the solubilized protein (FIG. 1).

(2) Molecular weight:

40,000 to 60,000 measured by SDS-polyacrylamide gel electrophoresis. In this instance, color development is not detected in the lower molecular weight area of several ten thousands in the gel, which are caused by hydrolysis of the protein during the treatment steps.

Figure 2:
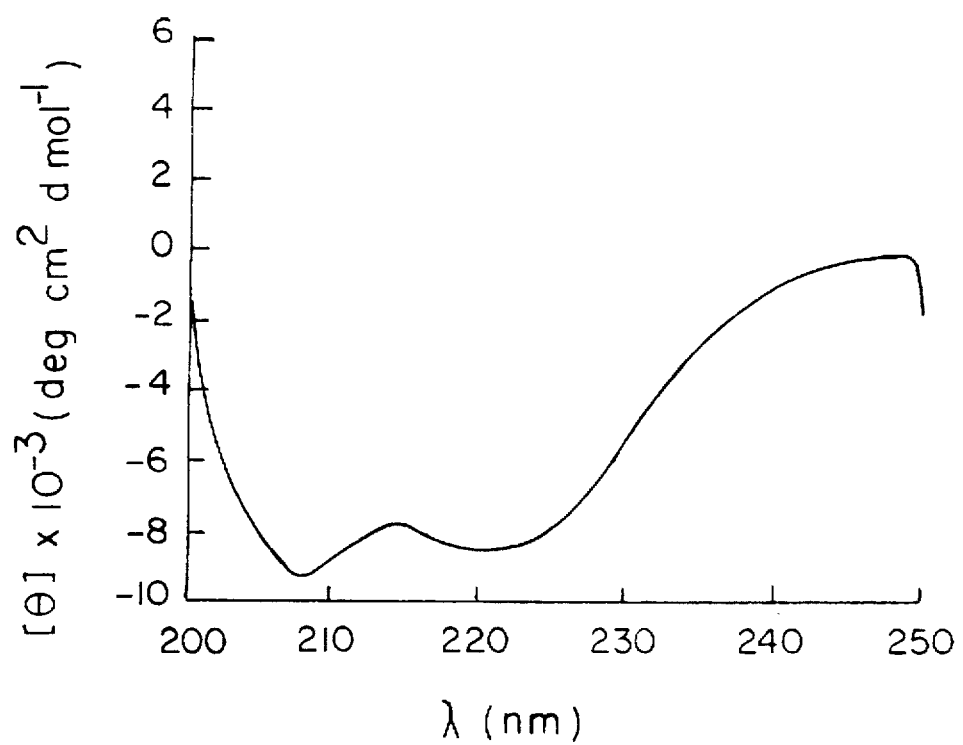
FIG. 2 is a graph showing the circular dichroism (CD) spectrum of a solubilized protein prepared by the process of the present invention.

(3) Circular dichroism (CD):

Negative peaks at 209 nm and 222 nm are detected, which indicates that the a-helix structure is formed in water (FIG. 2).

As is evident from the above results, the solubilized protein of the present invention has a structure in which mercapto groups (SH) formed by the cleavage of part or entire portions of disulfide bonds (—SS—) in the corresponding water-insoluble protein are replaced by carboxymethyldisulfide groups (—SSCH$_2$COOH).

Since these carboxymethyldisulfide groups do not return to cystine disulfide bonds under usual conditions, the solubilized protein can stably be preserved in solution for a prolonged period of time.

Although the solubilized protein prepared according to the process of the present invention is soluble in water, cystine disulfide bonds can be formed again under oxidative condition to regenerate a water insoluble —SS— cross-link structure.

In consequence, solubilized protein prepared according to the present invention can be used as a material for regenerated protein products, such as regenerated protein films and regenerated protein fibers of optional shapes that have the same properties as the original water-insoluble protein.

Such regenerated protein films and fibers may preferably be produced by a) a process in which solubilized protein prepared according to the process of the present invention is dialyzed against water directly or after its reduction with a reducing agent and then disulfide bonds are regenerated in or between polypeptides by oxidation, or b) by a process in which solubilized protein is molded into a film or a fiber, and then disulfide bonds are regenerated therein in the same manner as described above.

In addition, it is possible to produce composite materials by jointly using at the time of regeneration other available proteins, such as collagen, elastin, silk protein and other like proteins, natural high molecular compounds, such as polysaccharides and the like, and derivatives thereof or known solutions of synthetic high molecular compounds.

The solubilization process of the present invention produces solubilized proteins from water-insoluble proteins with a high efficiency. Also, since the reaction product is neither strongly alkaline nor strongly acidic, its after treatment can be carried out safely and easily.

Furthermore, the solubilized protein prepared according to the process of the present invention, namely a protein having carboxymethyldisulfide groups, is markedly useful as a material for producing regenerated protein products, such as regenerated protein films and regenerated protein fibers, because the original water-insoluble protein can be restored by molding the solubilized protein into an optional shape and then subjecting the moldings to reduction and subsequent oxidation to effect regeneration of disulfide bonds.

For example, a regenerated protein film may be obtained by a process comprising:

(i) spreading an aqueous solution of the solubilized protein onto a plate;

(ii) drying the aqueous solution spread onto the plate in step (i) to form a film of the solubilized protein;

(iii) reacting the film obtained in step (ii) with a reducing agent;

(iv) washing the film obtained in step (iii) with a mixed solvent of an organic solvent with water containing a plasticizer;

(v) drying the film obtained in step (iv); and (vi) peeling off the resulting regenerated protein film from the plate in the presence of water.

The concentration of the solubilized protein in the aqueous solution to be used in step (i) is preferably from 1 to 5% by weight. The aqueous solution may further contain a plasticizer in an amount of from 1 to 3% by weight.

As the plate onto which the aqueous solution of the solubilized protein is spread, various types of plates may be used and preferred examples thereof include Teflon plate, polypropyrene plates and polycarbonate plates.

The aqueous solution of the solubilized protein is spread onto the plate and then dried for 1 to 3 days, preferably over silica gel in a desiccator, to form a film.

Thereafter, the film is reacted with a reducing agent, whereby the carboxymethyldisulfide groups in the solubilized protein are reduced and converted into mercapto groups. The reaction is preferably carried out in a mixed solvent comprising water and an organic solvent in the presence of a plasticizer under a weakly alkaline condition (i.e., a pH of from 8 to 11). In this instance, it is preferred that a solution is prepared in advance by mixing the organic solvent and an aqueous solution of the reducing agent and adding thereto the plasticizer, and the reaction is carried out by spraying the solution onto the film of the solubilized protein or by immersing the film of the solubilized protein into the solution together with the plate. The reducing agent is preferably contained in the solution in the concentration of from 0.1 to 2M. The volume ratio of the organic solvent to the aqueous solution of the reducing agent to be mixed is preferably from 90/10 to 70/30. The plasticizer is preferably added to the solution in an amount of from 5 to 20% by weight. In general, the reaction is carried out for from 1/6 to 1/2 hour at room temperature.

After the completion of the reaction with the reducing agent, the film is washed with a mixed solvent of an organic solvent with water containing a plasticizer. The plasticizer is contained in the mixed solvent in an amount of 5 to 20% by weight. The volume ratio of the organic solvent to water to be mixed is preferably from 90/10 to 70/30.

Then, the film is dried in air at 80° to 100° C. for from 1/10 to 1/4 hour, whereby the mercapto groups in the film are oxidized and converted into disulfide bonds.

Thereafter, the film can be peeled off from the plate in the presence of water to obtain a colorless and transparent keratinous film. In this instance, the film may be immersed in water together with the plate and then peeled off from the plate in water. Alternatively, the film may be peeled off from the plate by washing it with water.

Examples of the plasticizer include methyl cellosolve, ethyl cellosolve, propyl cellosolve, Carbitol and glycerin, with glycerin being preferred. Examples of the organic solvent include methanol, ethanol, isopropanol, n-propanol and acetone, with methanol being preferred. Examples of the reducing agent include thioglycolic acid and thioglycol, with thioglycolic acid being preferred.

Since protein products having similar properties similar to human hair, nails, and skin tissues can be produced in optional shapes, solubilized protein according to the process of the present invention is also useful in the fields of cosmetics and medicines.

Moreover, it is possible to use solubilized protein prepared according to the present invention as a heavy metal capturing agent and the like, because it contains carboxymethyldisulfide groups in its structure and can be insolubilized when required.

The following examples are provided for the purpose of illustration of specific embodiments of the present invention, and are not to be construed as limiting the scope of the Invention. Unless otherwise indicated, all parts, percents and ratios are by weight.

EXAMPLE 1

A 1.0 g portion of Merino wool was treated at 30° C. for 3 hours with 50 ml of 0.2M thioglycolic acid aqueous solution which was adjusted in advance to pH 9.6 with 3M potassium hydroxide. Next, 24 g (8M in final concentration) of urea was added to the thus treated mixture and stirred at 30° C. for 24 hours to effect reduction. Thereafter, the resulting solution was adjusted to pH 7 by dropwise addition of acetic acid, followed by 3 days of oxidation treatment, which was carried out by moderate bubbling air into the reaction system. At this stage, the mercapto-specific odor disappeared.

The thus obtained solution was dialyzed using a dialysis membrane capable of separating molecules having a molecular weight of 10,000 or less, thereby removing urea and the like from the solution. Next, water insoluble materials that precipitated out during the dialysis step were separated by 10 minutes of centrifugation at 2,500 rpm to obtain a viscous solution of the water-solubilized wool keratin protein of interest.

After this solution was subjected to freeze drying, the weight of the resulting solubilized protein powder was measured and the solubilization ratio was calculated to be 51.4%. When the molecular weight of the solubilized protein was measured by SDS-polyacrylamide gel electrophoresis, two keratin protein-specific bands were detected on the gel at positions corresponding to molecular weights of 40,000 and 80,000. Color development in the gel corresponding to low molecular weight hydrolyzed protein products areas was not detected.

EXAMPLE 2

A 1.0 g portion of wool was treated at 30° C. for 3 hours with 50 ml of 1.0M 2-mercaptoethanol aqueous solution which was adjusted in advance to pH 10 with 3M potassium hydroxide. Next, the wool swelled by the reduction treatment was collected by filtration and mixed with 50 ml of 0.2M thioglycolic acid aqueous solution which was adjusted in advance to pH 10 with 3M potassium hydroxide. This was further mixed with 24 g (8M in final concentration) of urea and stirred at 30° C. for 24 hours to effect the reduction reaction. Thereafter, the resulting solution was adjusted to pH 7 by dropwise addition of acetic acid, followed by 2 hours of oxidation treatment at room temperature with dropwise addition of a 50 ml aqueous solution of 1M sodium bromate. At this stage, the mercapto-specific odor disappeared.

The thus obtained solution was dialyzed using a dialysis membrane capable of separating molecules having a molecular weight of 10,000 or less, thereby removing urea and the like from the solution. Next, water-insoluble materials that precipitated out during the dialysis step were separated by 10 minutes of centrifugation at 2,500 rpm to obtain a solution of the water-solubilized wool keratin protein of interest. After this solution was subjected to freeze drying, the weight of the solubilized protein powder was measured and the solubilization ratio was calculated to be 53%.

When the molecular weight of the solubilized protein was measured by SDS-polyacrylamide gel electrophoresis in the same manner as in Example 1, two keratin protein-specific bands were detected on the gel at positions corresponding to the molecular weights of 40,000 and 80,000. Color development in the gel corresponding to low molecular weight hydrolyzed protein products was not detected.

TEST EXAMPLE 1

Amino acid composition of solubilized wool keratin protein:

A 1.4 mg portion of the solubilized wool keratin protein solution obtained in Example 1 was hydrolyzed with 1 ml of 6N hydrochloric acid. It was then dried to a solid under a reduced pressure and then dissolved in 2 ml of 0.02N hydrochloric acid. Thereafter, a 10 ml portion of the thus prepared solution was analyzed by an amino acid analyzer (L-8500, manufactured by Hitachi, Ltd.). Results of the analysis are shown in FIG. 1.

As is evident from the results shown in FIG. 1, cystine-thioglycolic acid disulfide bonds, which do not exist in the original wool protein, are formed in the solubilized protein.

TEST EXAMPLE 2

Immunological activity against hard keratin antibody in human hair mother cells:

Solubilized protein was isolated in accordance with the SDS-polyacrylamide gel electrophoresis of Example 1 and subjected to a reduction treatment to obtain regenerated protein. The regenerated protein thus obtained was transferred on a polyvinyl difluorite membrane to examine its reactivity against the antibody prepared from hard keratin in human hair mother cells, in accordance with the procedure disclosed in *J. Cell Biol.*, vol.103, p.2593 (1987). The sample before the reduction treatment, which was a solubilized protein, showed no reactivity with the antibody, however, the disulfide bond-regenerated protein sample obtained after the reduction treatment showed a reactivity with the antibody.

TEST EXAMPLE 3

Measurement of circular dichroism (CD):

A 2 mg portion of the freeze-dried powder of water-solubilized wool keratin protein obtained in Example 1 was dissolved in 2 ml of ion-exchanged distilled water. Using a 1 mm cell, the circular dichroism of the thus prepared solution was measured within a wavelength range of from 200 to 250 nm using a CD/ORD spectrometer (Model A-20, manufactured by JASCO). The results are shown in FIG. 2.

As is evident from FIG. 2, the solubilized protein forms an a-helix structure in water, because the spectrum of its solution has negative peaks at 209 and 222 nm.

EXAMPLE 3

A 50 ml portion of 3M potassium hydroxide aqueous solution was added to 1.0 g of human hair to adjust the pH to 11. This was mixed with 50 ml of 0.2M thioglycolic acid aqueous solution and treated at 50° C. for 20 minutes, followed by the addition of 24 g (8M in final concentration) of urea. The solution was subsequently stirred at 30° C. for 24 hours to effect reduction reaction.

Thereafter, the resulting solution was adjusted to pH 7 by dropwise addition of acetic acid and subjected to 3 days of oxidation treatment, which was carried out by bubbling air into the reaction system to obtain an aqueous solution of solubilized keratin protein. At this stage, the mercapto-special odor disappeared.

The thus obtained solution was dialyzed using a dialysis membrane from which molecules having a molecular weight of 10,000 or less can be removed, thereby removing urea and the like from the solution. Next, water insoluble materials that precipitated out during the dialysis step were separated by 10 minutes of centrifugation at 2,500 rpm to obtain a solution of the solubilized hair keratin protein of interest.

When this solution was subjected to freeze drying, the weight of the resulting solubilized protein powder was measured and the solubilization ratio was calculated to be 31.7%.

EXAMPLE 4

Two % by weight of glycerin was added to a 3% by weight aqueous solution of a solubilized protein and the resulting mixture was spread over a Teflon plate. After drying the mixture to form a film on the plate, a solution which was prepared in advance by mixing 90% by volume of ethanol with 10% by volume of a 1M aqueous solution of thioglycolic acid (pH=9.0) and adding thereto 10% by weight of glycerin was sprayed onto the film. After allowing to stand for 10 minutes, the resulting film was washed by immersing it, together with the plate, in a solution which was prepared by mixing 80% by volume of ethanol and 20% by volume of water and adding thereto 10% by weight of glycerin. Thereafter, the resulting film was dried at 100° C. for 10 minutes and then washed with water, thereby obtaining a colorless and transparent regenerated keratinous film which swells but does not dissolve in water.

The number of cystine residues in the solubilized protein which was used for producing the regenerated keratinous film determined by an automatic amino acid analyzer was 29 per 1,000 amino acid residues. On the other hand, the number of cystine residues and cysteine residues in the resulting regererated keratinous film determined by means of polarography using mercury methyliodide were respectively 26 and 12.

The resulting regenerated keratinous film had a thickness of 20 μm, a Young's modulus of $10.0 \times 10^7$ N/m$^2$ under a relative humidity of 65% at a temperature of 20° C., a breaking strength of $3.5 \times 10^6$ N/m$^2$, and a breaking stretch of 15%.

While the invention has been described in detail and with reference to specific examples thereof, it will be apparent to one skilled in the art that various changes and modifications can be made therein without departing from the spirit and scope thereof.

What is claimed is:

1. A process for the production of a solubilized protein which consists essentially of:
   (a) treating a disulfide bond-containing water-insoluble protein material with an aqueous alkaline solution of a reducing agent and then treating with a protein denaturing agent; and
   (b) reacting said disulfide bond-containing water-insoluble protein material from step (a) with thioglycolic acid in the presence of an oxidizing agent under a weakly acidic to a weakly alkaline condition to convert disulfide bonds in said disulfide bond-containing water-insoluble protein material into carboxymethyldisulfide groups and thereby produce said solubilized protein, said process being conducted without any water washing step.

2. The process of claim 1, wherein said reducing agent comprises thioglycolic acid.

3. The process of claim 1, wherein said oxidizing agent comprises air or oxygen.

4. The process of claim 1, wherein said disulfide bond-containing water-insoluble protein material is selected from the group consisting of hairs, feathers, horns, hooves, and claws of animals.

5. A process for the production of a regenerated protein product from a solubilized protein which consists essentially of:
   (a) treating a disulfide bond-containing water-insoluble protein material with an aqueous alkaline solution of a reducing agent and then treating with a protein denaturing agent;
   (b) reacting said disulfide bond-containing water-insoluble protein material from step (a) with thioglycolic acid in the presence of an oxidizing agent under a weakly acidic to weakly alkaline condition to convert disulfide bonds in said disulfide bond-containing water-insoluble protein material into carboxymethyldisulfide groups and thereby produce said solubilized protein;
   (c) recovering said solubilized protein; and
   (d) forming said solubilized protein into a shape; and
   (e) regenerating disulfide bonds in said solubilized protein to produce said regenerated protein product, said process being conducted without any water washing step.

* * * * *